United States Patent
Grillari et al.

(10) Patent No.: US 9,157,907 B2
(45) Date of Patent: Oct. 13, 2015

(54) PANELS OF IMMORTALIZED MAMMALIAN CELLS AND THEIR USE

(75) Inventors: Johannes Grillari, Bisamberg (AT); Regina Grillari, Bisamberg (AT); Otto Kanzler, Boeheimkirchen (AT)

(73) Assignee: Universität für Bodenkultur Wien, Vienna (AT)

( * ) Notice: Subject to any disclaimer, the term of this patent is extended or adjusted under 35 U.S.C. 154(b) by 0 days.

(21) Appl. No.: 13/695,423

(22) PCT Filed: Apr. 27, 2011

(86) PCT No.: PCT/EP2011/056641
§ 371 (c)(1),
(2), (4) Date: Oct. 30, 2012

(87) PCT Pub. No.: WO2011/134989
PCT Pub. Date: Nov. 3, 2011

(65) Prior Publication Data
US 2013/0045892 A1    Feb. 21, 2013

(30) Foreign Application Priority Data

Apr. 30, 2010 (EP) .................................... 10161594

(51) Int. Cl.
*C40B 50/00* (2006.01)
*G01N 33/50* (2006.01)
(52) U.S. Cl.
CPC ............ *G01N 33/5044* (2013.01); *C40B 50/00* (2013.01); *G01N 33/5014* (2013.01)
(58) Field of Classification Search
None
See application file for complete search history.

(56) References Cited

U.S. PATENT DOCUMENTS

2003/0232752 A1* 12/2003 Freeman et al. ................ 514/12

FOREIGN PATENT DOCUMENTS

WO    2008/137031    11/2008

OTHER PUBLICATIONS

ATCC Cell Biology Catalogue 2007 (obtained from: https://www.lgcstandards.com/WebRoot/Store/Shops/LGC/MediaGallery/catalogues/ATCC_Cell_Biology_Catalogue_2007.pdf); cited pages attached.*
Sacco et al. (2004) "Cell-based assay for the detection of chemically induced cellular stress by immortalized untransformed transgenic hepatocytes" BMC Biotechnology 4:5.*
International Search Report, International Patent Application No. PCT/EP2011/056641, Jun. 14, 2011.
International Written Opinion, International Patent Application No. PCT/EP2011/056641, Jun. 14, 2011.
International Preliminary Report on Patentability, International Patent Application No. PCT/EP2011/056641, Nov. 6, 2012.
Extended European Search Report, European Patent Application No. 10161594.6-1223, Aug. 3, 2010.
American Type Culture Collection, "ATCC Cell Biology Catalogue", 2007.
Anderson K et al., Toxicology in Vitro, 10:721-727 (1996).
Bodnar AG et al., Science, 279:349-352 (1998).
Cai et al., J. Biol. Chem. 285:11227-11234 (2010).
Cellumen Inc., CellCiphr Toxicity Profiling Service Brochure, 2008.
Chang MW et al., Exp Cell Res., 309:121-136 (2005).
Cone R D et al., Molecular and Cellular Biology, 8(3):1036-1044 (1988).
Daniele N et al., Biochemical Society Transactions, 30(4):800-802 (2002).
Delvenne P et al., Vaccine, 19:2557-2564 (2001).
Dickson Mark A et al., Molecular and Cellular Biology, 20(4):1436-1447 (2000).
Elenbaas et al., Genes Dev., 15(1):50-65 (2001).
Esteban et al., Cell Stem Cell, 6:71-79 (2010).
Fichorova R N et al., Biology of Reproduction, Society for the Study of Reproduction, Champaign, IL, US, 57(4):847-855 (1997).
Forsyth et al., Neoplasia, 6:258-265 (2004).
Garcia-Escudero et al., Mol Ther., 18:394-403 (2010).
Geron Corporation "10-K Annual Report" (1999).
Griendling KK et al., Clin Exp Pharmacol Physiol., 15:105-112 (1988).
Guber Leonhard et al., "Characterisation of a new human renal proximal tubular cell line (RPTEC/TERT1), generated by the introduction of telomerase activity," 15th Congress on Alternatives to Animal Testing Linz 2008 & 12th Annual Meeting of MEGAT—Middle European Society for Alternative Methods to Animal Testing, 2008.
Harvard Skin Disease Research Center, "Human Skin cell lines in the Cell Culture Core collection," 2010.
Hooijberg et al., J. Immunol., 165:4239-4245 (2000).
Hosoya K-I et al., AAPS Pharmsci, 2(3):1-11 (2000).
Iype Lisa Elizabeth et al., Cytotechnology, Kluwer Academic Publishers, DO, 26(3):207-218 (1998).
Kowolik et al., Oncogene, 23:5950-5957 (2004).
Lowry and Plath, Nat Biotechnol., 26:1246-1248 (2008).
Madan Ajay et al., Drug Metabolism and Disposition, 31(4):421-431 (2003).
Meineke et al., Strahlenther Onkol., 180:102-108 (2004).
O'Malley et al., Curr Opin Biotechnol., 20:516-521 (2009).
Orosz et al., In Vitro Cell Dev Dio Anim., 40:22-34 (2004).
Ouellette M M et al., Human Molecular Genetics, Oxford University Press, Surrey, 9(3):403-411 (2000).

(Continued)

*Primary Examiner* — Tracy Vivlemore
*Assistant Examiner* — Karen S Weiler
(74) *Attorney, Agent, or Firm* — Michael Fedrick; Loza & Loza, LLP

(57) ABSTRACT

Panels of mammalian cell samples, kits and methods of use thereof. The panels comprise samples or sets of samples of immortalized primary cells, obtained from different tissues and organs of healthy and/or diseased donors. The cell panels are useful in assays for testing effects of drug candidates, e.g. for activity and toxicity.

4 Claims, No Drawings

(56) References Cited

OTHER PUBLICATIONS

Pang et al., Cancer Res., 69:518-525 (2009).
Racusen et al., J Lab Clin med., 129:318-329 (1997).
Rensen et al., Neth Heart J., 15(3), pp. 100-108 (2007).
Roig A I et al., Gastroenterology, 138(3):1012-1021 (2010).
Ryan et al., Kidney Int., 45(1), 48-57 (1994).
Salminen et al., Biochem Biophys Res Commun 394, 439-442 (2010).
Sinz et al., Drug Discovery Today: Technologies, Elsevier, 3(1):79-85 (2006).
Song et al. Cell Res. 19(11):1233-1242 (2009).
Stadler et al., Cytotherapy, 9:488-498 (2007).
Steen David, Current Separation, 20(4):137-140 (2004).
Takahashi and Yamanaka, Cell, 126:663-676 (2006).
Tsai and Chou, J Biomed Sci., 16:68 (2009).
Vaughan et al., Differentiation, 74 (4):141-148 (2006).
Voglauer et al., Int J Oncol., 26:961-970 (2005).
Voglauer et al., Exp Cell Res., 312:746-759 (2006).
Voss C et al., Toxicology and Applied Pharmacology, 211 (3):177-187 (2006).
Waki Koji et al., Cancer Science, 101(7):1678-1685 (2010).
Waiters Raymond L et al., Radiation Research, 172(1):82-95 (2009).
Wege et al., Gastroenterology, 124:432-444 (2003).
Wieser Matthias et al., American Journal of Physiology—Renal Physiology, 295(5):F1365-F1375 (2008).
Wiesner et al., PLoS One, 3(1), e1464 (2008).
Wilmer et al., Cell Tissue Res., 339:449-457 (2010).
Wolbank et al., Tissue Eng Part A 15, 15(7):1843-1854 (2009).
Zhu et al., Aging Cell, 6:515-523 (2007).

* cited by examiner

PANELS OF IMMORTALIZED MAMMALIAN CELLS AND THEIR USE

CROSS-REFERENCE TO RELATED APPLICATIONS

This application is the U.S. national stage of International Patent Application No. PCT/EP2011/056641, filed on Apr. 27, 2011 and entitled PANELS OF IMMORTALIZED MAMMALIAN CELLS AND THEIR USE which claims the benefit of priority under 35 U.S.C. 119 from patent application Ser. No. 10/161,594.6 EP, filed Apr. 30, 2010. The disclosures of the foregoing applications are incorporated herein by reference in their entireties.

The present invention relates to panels comprising immortalized mammalian cells and methods of using them, in particular in assays for testing candidate compounds during drug development.

The development of novel therapeutics is labour and cost intensive. Moreover, it is often delayed due to the fact that promising drug candidates fail at late development stages, sometimes as late as in clinical phase II trials, which results in high attrition rates and unnecessarily high additional costs. Therefore, it is desirable to improve pre-clinical testing of novel compounds to avoid any such unnecessary delay and costs and to be able to better predict and generalize the therapeutic strategies. To this end, a maximum of information on the properties of drug candidates should be available as early as possible in the development process.

Attempts to this end are reflected in the concept of pharmacogenomics and pharmacogenetics, where the transcriptional profiles and genomic basis of patients are correlated with the efficacy of drugs.

With the accumulation of knowledge in the field, it has become apparent that information gained from assays employing cells from a single individual or employing transformed cell lines, which have properties that are usually not representative for the in vivo situation in an individual, is of only limited value for assessing or predicting a compound's activity and potential toxicity in the human physiological setting.

Therefore, there is a need for new methods of assessing the properties of compounds during drug development.

In order to provide assays with cells that have a normal karyotype, WO2008/137031 suggests a panel of biological samples comprising at least five genetically diverse biological samples from a given species, wherein the samples are tissues, primary cells or stem cells.

This approach has the downside that primary cells have a limited life span due to telomere shortening at each round of cell division. Therefore, reproducibility is limited, because the panels of primary cells have to include different donors after the replicative potential of cells has been exhausted during large scale screenings.

It has been an object of the invention to overcome the deficiencies of the available methods and of the biological samples used therein and to provide novel panels of cells as well as assays employing them.

Therefore, in a first aspect, the present invention relates to a panel of mammalian cell samples, wherein a) said cell panel comprises cell samples of immortalized primary cells, wherein said samples are present as
  i) cell samples or sets of cell samples from organs and/or tissues of at least three healthy donors and cell samples of the corresponding cell types from at least three diseased donors, and/or or cell samples from at least three healthy donors of at least two different age classes, and/or skin cell samples from donors of at least two different skin types; or as
  ii) a set of cell samples from different organs and/or tissues from one healthy or diseased donor; and wherein
b) said panel further comprises at least one cell sample comprising kidney cells and/or liver cells and/or blood cells and/or endothelial cells and/or skin cells.

The term "panel" shall mean a pre-defined combination or array of cell samples or sets of cell samples.

The term "set of cell samples" shall mean a pre-defined combination or array of cell samples. A set may comprise cell samples from the same or from different organs from one or more donors.

A "cell sample" shall mean a number of cells comprising cells of the same cell type.

A cell sample of immortalized cells may comprise immortalized cells in the form of a mass population, when individual clones arising after immortalization are not separated from each other, i.e. a population containing several clonal subpopulations. The immortalized cells of a cell sample may also be monoclonal, i.e. comprise cells of a single clone that has arisen after immortalization. Within a set of cell samples both types of cell populations may be present. Mass-cultured populations from individual donors have the advantage that they better reflect the in vivo situation of a tissue, as opposed to a monoclonal culture in the case that it may have arisen from an individual cell within a tissue that is not representative for the totality of the cells, e.g. in that it is less sensitive to the test compound than the majority of cells. Thus, the data of an assay using such monoclonal culture may deviate from the correct result. On the other hand, monoclonal populations have the advantage that assays have a higher reproducibility, and if more than three monoclonal cell samples are present in one set, the individual sensitivity of single cell clones is amenable to statistical analysis. Depending on the issue of interest to be resolved, e.g. with respect to selected tissues, the skilled person is able to choose whether to include mass populations or monoclonal populations or mixtures thereof in the sets of cells that form the cell panels of the invention.

The number of cell samples in a set of cells according to embodiment i) is preferably 1-5, in embodiment ii), it is usually 3. Limitations as to the number of cell samples are not due to technical reasons with regard to generating a set or panel of cell samples, but due to the usually limited availability of cell samples from a single individual. The number of cell samples may however be higher, e.g. when, in exceptional cases, a greater number of tissue samples is available from a single individual. The number of cell samples in a set may also be higher when cells of a certain cell type are present in a set both in the form of a mass population and of a clonal population—in this case, each such population is to be considered a distinct cell sample.

Depending on the intended use, the number of cells in a cell sample may vary in a wide range from one cell up to $10^{15}$ cells (the high cell number defined by the upper limit is relevant if it is required, for special purposes, to cultivate the cells), preferably from $10^3$-$10^6$ cells. By way of example, for use in a high-throughput screening assay employing adherent cells using a 96 or 384 well plate, the number of cells depends on the aim of the performed assay, the cell type, its size and its growth rates, typically between 100 and 5000 cells/cm$^2$.

In the meaning of the present invention, the term "cell type" is used as acknowledged in the field, i.e. a distinct morphological or functional form of cell, as obtained during cellular differentiation in vivo or in vitro. A distinct cell type, for the purpose of the present invention, may be obtained from an organ or tissue as well as by differentiation from stem cells or progenitor cells, including induced pluripotent stem cells (iPSCs).

Immortalized cells are cells that have been immortalized in culture by inserting genes into the cells that prolong their life span and/or by inactivating genes that shorten their life span. Standard protocols are based on inserting the simian virus 40 (SV40), expressing the Telomerase Reverse Transcriptase protein (TERT), co-expressing the hTERT catalytic subunit with either p53 or RB siRNA, or overexpressing Ras or Myc T58A mutants. "Immortalized cells" designates cells with a replicative life span that has, upon introduction of the immortalizing agents or genes, at least doubled.

Although normal human diploid cells normally do not spontaneously immortalize in culture, but instead enter replicative senescence after a finite number of population doublings, spontaneous immortalization of human cells has been observed in vitro, however, as an extremely rare event (Forsyth et al., 2004). In the case that such cells are available, they may also be present in one or more cell samples in the panel of the present invention. Spontaneously immortalized cells may also be present in the case that the cells are from other mammalian species, e.g. from mouse, where spontaneous mutations are more frequent than in humans.

As opposed to primary cells, immortalized cells have the advantage that they are available in almost unlimited amounts and allow to conduct large scale screening assays in a reproducible way, including high-throughput as well as high content screening in large-scale, miniaturized screening assays or assays for profiling a candidate compound in drug development.

The immortalized cells are derived from cells obtained from different tissues/organs of various healthy and/or diseased donors. In the case that the panel comprises sets of cell samples from different donors, in order to exclude the variability of genetic background, a cell panel of the invention comprises preferably cell samples from at least five different donors. Since the efficacy of a drug may depend on the age of the patient to be treated, it may be advantageous to provide cells from donors of different age classes. For the purpose of the present invention, the age classes may be defined as follows: neo-natal (0-1 years), pre-pubertal (2-12 years), young (13-18 years), middle-aged (35-55 years), elderly 65-99 years), centenarians (>100 years).

Due to the variability of a statistically relevant number of tissues and donors, it is possible, by means of the present invention, to gain a maximum of information, e.g. on a test compound's effects, especially in regard to efficacy and side-effects on a cellular level.

The cells of the panel of the invention are preferably human cells, however, the panel may also be comprised, totally or in part, of other mammalian cells, in particular cells from animals that are commonly used as model organisms in preclinical development, e.g. rodent cells (e.g. mouse or rat) or monkey cells (e.g. Cynomolgus).

A panel of cells may comprise sets of cells from different species, however, a set of cell samples preferably comprises cells from a single species.

The cell panels, including cell samples or sets of cells, are usually tailor-made as requested by a customer in terms of cell type, number of cell samples/sets and donors (expediently at least five). Typically, the cell types are selected from one or more of fibroblasts, epithelial cells of various organs (e.g. kidney, mammary, retina, pancreas, esophagus, bronchia, alveola, ovary, tonsil), myoblasts, endothelial cells, cardiomyocytes, blood cells (B cells can be immortalized by IL-4 (Wiesner et al., 2008), T-cells by telomerase after stimulation with antigens (Hooijberg et al., 2000)), keratinocytes, osteoblasts, urothelial cells, fetal liver cells, Schwann cells, neural progenitor cells, Sertoli cells, and urine-derived cells including e.g. HEPTECs (human exfoliated proximal tubular epithelial cells).

Tumor cells and/or cells from other diseased tissues also may be part of the cell panel of the invention to test for efficacy of drug candidates, again using cells from a statistically relevant number of patients.

As mentioned above, methods for immortalizing primary cells are known in the art, e.g. exemplified by the immortalization of RPTECs, which relies on the use of viral oncogenes, like HK-2 with HPV16 E6/E7 (Ryan et al., 1994) or HKC with a hybrid adeno-12-SV40 virus (Racusen et al., 1997). More recently, SV40 with or without hTERT overexpression has been used (Kowolik et al., 2004; Orosz et al., 2004). A method for immortalizing umbilical vein endothelial cells (HUVECs) by hTERT over-expression is described by Chang et al., 2005.

In order to immortalize cell types for which immortalization protocols have not been published, routine experiments can be performed including medium optimization, e.g. using the recently developed protocol (Stadler et al., 2007) and overexpression of hTERT alone or in combination with SV40 large T and/or small t (Elenbaas et al., 2001), Bmi1 (Garcia-Escudero et al., 2010), CDK4 (Zhu et al., 2007), siRNA against p21, p16, c-myc, etc.

In certain embodiments, the immortalized cells are defined by at least one key functional or morphological property that they have in common with the parental primary cells that they are derived from or a corresponding primary cell. For the purpose of the present invention, the immortalized primary cells must fulfil the requirement that they are, with respect to certain cell-type-specific properties as close to primary cells as possible, i.e. in their characteristic morphological and functional properties. To this end, the cells contained in the panel of the invention have been compared, preferably with their respective parental primary cells, with regard to at least one essential property (or "key property"), i.e. they have been tested as to whether they correspond to or are as close as possible to the parental cells with respect to such property.

In particular, a "key property" is a property that is essential for the bioassay to be conducted with the cell. By way of example, if cells are to be employed in an assay in which the effect of a test compound on a target molecule of interest is to be determined, cells are selected that express said target molecule at a level that is comparable with that of the primary cells. Examples of other properties are the potential to differentiate, the capacity for the uptake of certain molecules (e.g. ions like $Ca^{2+}$), the cells' capacity to undergo apoptosis, etc. In the case of RPTECs (renal proximal tubule epithelial cells), the cells may be tested for formation of tight junctions and domes, expression of aminopeptidase N, cAMP induction by parathyroid hormone, sodium-dependent phosphate uptake, and the megalin/cubilin transport system, as described by Wieser et al., 2008. The immortalized cells may also be tested for marker proteins that are typical for a given cell type, e.g. epithelial markers like van Willebrand factor (which can be detected e.g. by indirect immunofluorescence microscopy), for their response to inflammatory signals, e.g. TNF-α, by measuring the inducibility of different cell adhesion molecules (as measured by flow cytometry), or for their differentiation and neoangiogenic potential, as described for HUVECs by Chang et al., 2005. Furthermore, the karyotypes of the immortalized cells can be routinely tested for by Giemsa banding of mitotic spreads and chromosomal aberration in order to demonstrate genomic stability and the maintenance of highly differentiated phenotypes.

In certain embodiments, the properties of the immortalized cells are compared with data of reference primary cells in a database that contains, beside the donors' data, a reference profile of the parent primary cells' key properties.

Depending on the cell types, the immortalized cells are cultivated as mono-cultures on appropriate substrates for cell adherence (Chang et al., 2005) or as suspension cells (Hooijberg et al., 2000). Immortalized cells can however also be used in 3D cultures (Vaughan et al., 2006), in co-cultures or in organoid cultures and tissue equivalents (Delvenne et al., 2001; Meineke et al. 2004).

In certain embodiments, the panel may contain, according to a), in addition to immortalized primary cells, embryonic stem cells, immortalized adult stem cells and/or progenitor cells like hematopoietic progenitor cells and/or other bone marrow-derived cells, urine-derived stem cells, endothelial progenitor cells, umbilical cord blood cells, and/or stem cells derived from adipose tissue or from amnion. Alternatively to stem cells as such, or in addition to stem cells, cells of different types may be included that have been obtained by differentiation of stem cells; examples are cardiomyoctes, hepatocytes, osteoblasts, adipocytes, b-cells of pancreas, keratinocytes, fibroblasts, neuronal cells.

In certain embodiments, the stem cells are iPSCs (induced pluripotent stem cells), which are stem cell-like cells derived from somatic cells by reprogramming. Including stem cells and iPSCs as well as cells that have been differentiated from these cell types in the panel is useful in cases e.g. if biopsies of specific tissues are not available or if specific cell types or tissues are not amenable to be isolated by known methods (e.g. if the cell type of interest is overgrown in vitro by other cell types within the tissue). In this case iPSCs can be established from other cell types (typically from fibroblasts or epithelial cells, or from urine-derived cells), which then can be differentiated into the cell type of interest that is to be included in the cell panel of the invention. iPSCs can be generated from various sources, including fibroblasts, hepatocytes, epithelial cells and adult human stem cells, according to methods known in the art (Cai et al., 2010; Esteban et al. 2010) and reviewed recently (Lowry and Plath, 2008).

According to certain embodiments, the somatic donor cells from which the iPSCs are derived are exfoliated cells from the urinary tract that are present in urine ("urine-derived cells"; in the following, iPSCs derived from urine cells are termed "UiPSCs"). To serve as donor cells for generating UiPSCs, the urine-derived cells may be of any cell type found in urine that is amenable to reprogramming, usually epithelilal or fibroblastoid cells. Obtaining UiPSCs can be done by expanding urine cells and differentiating them by reprogramming to become UiPSCs. The UiPSCs are then differentiated into the cell type of interest. Alternatively, cells may be used that have been obtained by direct reprogramming of urine cells to become differentiated cells of interest.

In order to reprogram the somatic cells, e.g. urine-derived cells, to become iPSCs, various methods known in the art can be performed, and several variations of the original "Yamanaka" protocol (Takahashi and Yamanaka, 2006), which uses four transcription factors (Oct3/4, Sox2, Klf4 and c-Myc), are by now available, including different strategies for delivering the necessary factors to the cells, including vectors based on expression plasmids, retroviral, lentiviral, or adenoviral vectors, piggyback transposons or episomal vectors. The factors can also be directly transduced as proteins by protein transduction or as mRNAs. Furthermore, various chemicals, e.g. vitamin C, can be added to replace the transcription factors or to reduce the number of transcription factors necessary for reprogramming. These methods have been reviewed recently (O'Malley et al., 2009).

The cell panel of the invention comprises at least 30%, in more preferred embodiments more than 50%, in even more preferred embodiments more than 70% immortalized primary cells.

In certain embodiments, the immortalized cells, iPSCs or cells obtained therefrom by (re)differentiation, may be genetically modified or may carry naturally occurring mutations, e.g. as present in cells that have been obtained from patients. For example, as suggested in WO 2008/137031, the cells can be mutagenized chemically, by radiation, or they may carry spontaneous mutations. Exemplary genetic modifications include, for example, those that result in a gain of function or loss of function, that are deletions or disruptions of specific genes or DNA regions, replacements of DNA sequences by homologous recombination, overexpression of one or more genes, and down-regulation, e.g. by RNA interference (RNAi), siRNA knockdown, shRNA, microRNA or silencing.

In certain embodiments, the cells may be genetically engineered to overexpress one or more proteins that are target molecules of interest for an intended therapy, e.g. cellular receptors for testing a compound for its antagonistic effect on activation of such receptor. In certain embodiments, the cells in the panel of the invention are derived from primary cells obtained from transgenic, knock-out, knock-in, knock-down, or other genetically modified animals. In certain embodiments, the primary cells can be engineered to express one or more reporter molecules (e.g. proteins that produce detectable signals such as fluorescence, bioluminescence, or positron emission tomography (PET) signals). Reporter molecules are well known in the art, examples are, as also suggested in WO 2008/137031, luciferase, green fluorescent protein (GFP), GFP derivatives, blue fluorescent protein (EBFP, EBFP2, Azurite, mKalama1), cyan fluorescent protein (ECFP, Cerulean, CyPet), yellow fluorescent protein derivatives (YFP, Citrine, Venus, YPet), chloramphenicol acetyltransferase (CAT), beta-galactosidase, or alkaline phosphatase. Reporter molecules can be utilized, for example, as a read-out for various assays or as a means to examine a signaling pathway (for example GPCR signaling, TGF-beta signaling, kinase activation, or other specific pathways).

For genetically engineering, the DNA molecules of interest may be introduced into the parent primary cells or, usually, into the immortalized cells using methods known in the art, such as, for example, lipofection, calcium phosphate co-precipitation, electroporation or viral vectors (e.g. adenovirus, lentivirus, retrovirus).

The cell samples contained in the panel according to b), also termed "toxicity index cells" herein, are cells that are indicative of a possible toxic effect, e.g. of a test compound, to the target cells, i.e. the cells according to a). The toxicity index cells may, but need not necessarily be immortalized primary cells but may also include primary cells, or established tumor cell lines like HepG2 or PC-2 cells. In the case that the toxicity index cells are liver cells, they may be hepatocytes that have been obtained by differentiation of stem cells or iPSCs, e.g. urine-derived iPSCs (UiPSCs).

For cosmetical testing, the same toxicity index cells as for pharmacological testing may be used; in addition, skin cells may be used. In principle, a toxicity index cell may be any cell that is involved in transportation by blood or in excretion.

In a further embodiment, the invention relates to a method for preparing a panel of mammalian cell samples for solving a biological problem of interest by means of a bioassay, said method comprising the steps of i) providing immortalized primary cells from tissues and/or organs that are relevant for said problem of interest, wherein said tissues and/or organs are from one or more healthy and/or diseased donors;
ii) selecting, from the cells obtained in step i), cells that are, with respect to at least one functional or morphological key property that is relevant for the read-out of said bioassay, identical with or closely similar to such property of the corresponding primary cells;
iii) providing cell samples comprising the cells selected in step ii);
iv) providing cell samples comprising kidney cells and/or liver cells and/or blood cells and/or endothelial cells and/or skin cells;
v) combining different cell samples of step iii) to form sets of cell samples; and
vi) combining different cell samples of step iii) and/or sets of cell samples of step v) with cell samples of step iv) to form a panel of cell samples.

The "corresponding primary cells" in step ii) may be selected from the parental primary cells from which the immortalized cells are derived or from reference primary cells, e.g. based on reference data that can be retrieved from a database.

By way of example, the biological problem may be determining the cytotoxicity of compounds; in this case the bioassay is a cytotoxicity assay and the toxicity index cells according to b) (representing the cell samples of step iv) are selected from kidney and/or liver cells to determine kidney and/or liver cytotoxicty. Examples for further biological problems and bioassays are given below in the context with the assays.

In a further embodiment, the present invention relates to an in vitro method for evaluating the effect of at least one test compound, or of a stimulus, on cell samples of immortalized primary cells of a cell panel, comprising the steps of i) contacting said cell samples with said test compound or stimulus;
ii) determining at least one response of said cell samples to said compound or stimulus; and
iii) evaluating the effect of said compound or stimulus by comparing the responses of each of the cell samples;
iv) determining a possible toxic effect of said compound or stimulus on liver cells and/or kidney cells and/or blood cells and/or endothelial cells and/or skin cells.

The effect of the compound or stimulus may, for example, be its effect on the expression or activation of a biological target molecule, e.g. a receptor, its efficacy, its toxic or adverse effects, ADME properties (absorption, distribution, metabolism and excretion). The assays of the invention are also useful for studying the mechanism of action as well as the pharmacokinetic and/or pharmacodynamic properties of a compound of interest. In the case that the cell samples are derived from a single diseased patient, the assay may be useful for designing a personalized treatment of such patient with a drug that best meets the individual therapeutic needs.

The assay of the invention may be run in laboratory scale or in the high-through-put format, the latter e.g. in the form of a primary screening assay.

Furthermore, the method of the invention may be useful for testing the reaction of the test cells to a physical stimulus, e.g. radiation, light, heat, shear forces, magnetic fields.

Assays of the invention are, inter alia, useful in research and development and for selecting or validating a therapeutic target. Examples of useful bioassays are well known in the art, e.g. those suggested in WO 2008/137031, like proliferation assays (MTT, XTT, BrdU incorporation, flow cytometry using DNA stains, staining for cell proliferation associated proteins like PCNA), cell cycle arrest (e.g. immunoreactivity to p21 or p16 antibodies), differentiation (assay of specific differentiation marker proteins by indirect or direct immunofluorescence microscopy or flow cytometry, assay for $Ca^{2+}$ deposition, for lipid droplet deposition, neuronal cell phenotype, etc.), assays for cell death and cytotoxicity (apoptosis or necrosis using DNA dyes (propidium iodine) and annexin V staining, TUNNEL assay, distribution of G1 peaks in flow cytometry, angiogenesis (matrigel assay, spheroid based assay,) enzymatic assays, test for neutralizing antibodies (e.g. against virus infection) and other substances (e.g. neutralization of toxins), VSV-Interferon assay, virus-based assays, resistance to stress, drug resistance, signal transduction (using reporter assays, e.g. based on bioluminescence). Assays of the invention are also useful for testing compounds in the cosmetics industry, in this case, according to embodiment ii) the cells are skin cells from donors of different skin types, preferably, the skin cells are fibroblasts and/or keratinocytes.

The assays of the invention may be used in differential drug screening" (DDS) assays. To this end, the cell panels contain target cells (the cells according to a), i.e. immortalized primary cells (optionally complemented by iPSCs and/or cells obtained from them by redifferentiation) that deliver the biological read-out of interest (e.g. indicating the efficacy of a test compound). In addition, cells according to b) are included for evaluating the cytotoxicity of the test compound ("toxicity index" cells), typically, kidney cells like RPTECs or HEPTECs or liver cells like human fetal hepatocytes.

In the case that toxicity testing is done for evaluating toxicity to the vascular system, the toxicity index cells are blood cells (usually T cells, B cells or macrophages), endothelial cells, and/or vascular smooth muscle cells. Toxicity testing is done together with efficacy testing, i.e. the toxicity index cells are contained in the cell panel together with the target cells, i.e. the immortalized primary cells, optionally supplemented by stem cells, as defined herein, and/or cells obtained by differentiation of stem cells. Alternatively, if only toxicity testing, without efficacy testing, is of interest, a cell panel may be used that specializes on toxicity testing, i.e. comprises a pre-defined combination of toxicity index cells.

In the Examples described herein, immortalized primary cells and assay methods are exemplified for testing candidate drugs as anti-tumor agents or as anti-diabetics.

Based on the assay results, calculating an efficacy/toxicity index may be useful for decision making on whether or not to proceed with the development of a candidate compound and/or for re-defining the development criteria for a potential successor compound.

The method of the invention may also be used for assessing the validity of an animal model for testing a drug candidate. In this case, by way of example, the responses of human cells and animal cells, e.g. mouse cells, of the same cell type to a test compound are compared. If the responses are identical or highly similar, the mouse may be considered a valid model for the issue of interest to be resolved.

According to another aspect, the invention provides a kit comprising, as its components, one or more cell panels or sets of cells of the invention.

A "kit," as used herein, typically defines a package, array, assembly or container including one or more of the panels or sets of the invention, and/or other components, e.g. the appropriate culture media, as well as instructions. The samples may be provided in frozen form or as cultures.

In certain embodiments, the kit contains one or more sets of cell samples, as defined herein, to be used by a customer as modules for putting together a cell panel of the invention.

A kit containing cell panels or sets of cells usually comprises, as its components, cell samples contained in suitable receptables, e.g. glass vials. In certain embodiments, the kit may comprise a cell panel comprising at least 10, 20, 30, 40, 50, or 100 cell samples. The kit may be provided in a multi-well plate format, e.g., in one or more 4, 12, 24, 48, 72, 96, 384, or 1536 well plates.

Additional components are, without limitation, diluents, salts, buffers, chelating agents, preservatives, drying agents, antimicrobials, growth factors, needles, syringes, packaging materials, tubes, bottles, flasks, beakers, and the like. The components are in a container, stored and shipped at room temperature, chilled, in liquid nitrogen or on dry ice. Instructions may include instructions for culturing, using, modifying, mixing, diluting, preserving, assembling or storing the cell samples and/or other components. The instructions may also include instructions for a specific assay to be performed with the cell samples, e.g. their use in screening assay. Instructions may be also be in the form of directions to a website, they may also contain links to computer systems and/or computer memory storage devices. The instructions may contain protocols to thaw the cells and plate the cells at a specific density, before performing a certain assay, e.g., apoptosis assay, proliferation assay, etc. in various formats.

The kit may also contain a quality certificate for the cell samples, e.g. based on a collection of data that allows comparing the properties of the immortalized cells with those of corresponding primary cells.

EXAMPLES

All procedures described herein are in accordance with the Declaration of Helsinki, and informed consent of patients is obtained. Whenever appropriate, the protocols and experimental designs are submitted to an independent ethics commission. Tests for absence of mycoplasma are routinely performed to guarantee high quality.

Materials and Methods

Retroviral Vectors and Cell Line Establishment

The hTERT-encoding cDNA is excised from plasmid pGRN145 (Bodnar et al., 1998) using EcoRl, ligated into the retroviral vector pLXSN (Clontech, Mountain View, Calif., USA) or into non-viral vector pCl-neo (Promega). Generation of retroviral particles and infection of cells is performed as described previously (Wieser et al., 2008). Transfection of cells using non-viral vectors is performed using lipofectamin 2000 or nucleofector technology (Amaxa biosystems) as described (Chang et al., 2005). 24 h post infection or transfection cells are passaged 1:3 in medium containing 100 µg/ml G418 to select for positive transfectants.

1. Generation of Cells

1.1. Human Dermal Fibroblasts (HDFs)

Fibroblasts derived from patients or healthy donors are used to establish immortalized cell strains (fibroblasts derived from Williams Beuren syndrome cells). The Williams-Beuren syndrome (WBS, also known as Williams syndrome, OMIM 194050) is a non-hereditary syndrome which occurs at random and can effect brain development in varying degrees associated with multiple symptoms, including characteristic congenital pattern of malformation and physical problems. WBS1 cells are isolated from skin biopsies. Cells are maintained in DMEM medium (Biochrom AG) supplemented with 10% FCS (PAN) and 4 mM L-glutamine and are routinely passaged by trypsinization at a 1:2 or 1:3 split ratio once or twice a week, depending on their growth potential. The medium of pre-senescent cultures is renewed twice a week. Cells are incubated at 37° C. in a humidified atmosphere with 5% $CO_2$.

The WBS1-hTERT and WBS1-neo cells are established by infection of WBS1 with recombinant retroviruses. Cells are routinely passaged by trypsinization at a 1:2 or 1:3 split ratio twice a week and are incubated at 37° C. in a humidified atmosphere with 5% $CO_2$.

In order to evaluate the similarity of the obtained cell strains to their parental primary cells, at least three prime characteristics are tested besides the presence of typical fibroblastoid morphology. In the case of fibroblasts, the cells are tested for the presence of fibroblast marker proteins fibroblast-specific protein 1 (FSP1), and prolyl-4-hydroxylase versus absence of epithelial marker proteins like immunoreactivity to pan cytokeratin antibody by flow cytometry and/or indirect immunofluorescence. More than 90% of the cells show homogenous distributions of these markers.

1.2. Tumor Cells

A cell line designated LOHG-F is established by mechanical dissociation of fresh fibroma tissue from a patient diagnosed with MEN1 (Multiple Endocrine Neoplasia Type 1). LOHG-F cells, as well as transfectants, are grown in a 1:1 mixture of DMEM/Ham's F12 medium (Biochrom KG), supplemented with 4 mM L-glutamine and 10% (v/v) fetal bovine serum (FBS; Hyclone Laboratories, Inc.) and 100 µg/ml G418 in the case of LOHG-F hTERT transfectants. Cells are subcultured at a 1:2 to 1:8 subculture ratio once or twice a week, depending on confluence and the population doubling (PD) level. For the calculation of PD, LOHG-F cells are designated PD0 at the time of first passage. Subsequent PDs are calculated as a function of passage number and splitting ratio. Normal human diploid skin fibroblasts (HDF5) and human SV40 ER-transformed skin fibroblasts (HF6) are grown in a 1:1 mixture of DMEM/Ham's F12 supplemented with 4 mM L-glutamine, 10 and 5% FBS, respectively. For introduction of hTERT, LOHG-F cells (PD24) are infected with recombinant retroviral particles, conferring overexpression of hTERT (Voglauer et al., 2005). Transfectants are selected 24 h post-infection using 100 µg/ml G418, and the clones are grown as a mass culture designated T1-LONG. Transfection of LOHG-F cells (PD26) with the plasmid pDEPT, conferring overexpression of SV40 Large T and small t proteins, is performed using Lipofectin (Gibco BRL) according to the manufacturer's protocol. After approximately two weeks, colonies expressing SV40 ER can be easily distinguished from surrounding LOHG-F cells by their morphology and growth characteristics. These cells are cultivated as mass culture and designated SV1-LOHG.

1.3. Endothelial Cells

Human umbilical vein endothelial cells (HUVECs) are isolated by collagenase treatment. The cells are cultivated in gelatin pre-coated flasks in M199 with Earle's salts supplemented with 4 mM glutamine, 15% fetal calf serum (FCS) and 10% endothelial cell growth supplement (EGGS) containing 170 U/ml heparin, at 37° C. in a humidified atmosphere with 5% $CO_2$. Cells are passaged once or twice a week at a split ratio of 1:2 to 1:8 according to the growth rate. HUVECs at PDL 18 are transfected with the plasmid DNA containing hTERT and a vector control by nucleofection (HUVEC Nucleofector™ kit, Amaxa biosystems) and stable transfectants (HUV-T-ECs) are selected by addition of 20 μg/ml G418 to the medium. In addition, overexpression of SNEV by retroviral vectors doubled the life span of HUVECs (Voglauer et al., 2006).

Confirmation of primary-cell like characteristics is obtained by testing the ability to form neoangiogenic webs in matrigel assays and the response to TNF-α and LPS in regard to induction of ICAM and PECAM, as well as determining expression of von Willebrand factor in Weibel-Pallade bodies, as described (Chang et al., 2005).

1.4. Vascular Smooth Muscle Cells (VSMCs)

VSMCs from healthy individuals or diabetic patients are grown in smooth muscle growth medium (SmGM-2) supplemented with the necessary growth factors (insulin, human fibroblast growth factor, human epidermal growth factor; Bio-Whitaker, San Diego, Calif.) in a humidified incubator at 37° C. with 5% $CO_2$. For introduction of hTERT, VSMCs are infected with recombinant retroviral particles as described above for fibroblasts. Transfectants are selected 24 h post-infection using 100 μg/ml G418, and the clones are grown as a mass culture, or single clones are isolated. For confirmation of maintenance of VSMC characteristics, specific markers are detected by flow cytometry and indirect immunofluorescence, i.e. a-smooth muscle actin, SM22a (Rensen et al., 2007) as well as the cells' response to angiotensin II (Griendling et al., 1988).

1.5. Renal Proximal Tubular Epithelial Cells (RPTECs)

Within 24 hours after surgery, tissue from the renal cortex of healthy individuals is fragmented and digested. After being passed through a 105 μm nylon mesh the filtrate is centrifuged, washed twice with phosphate buffer saline (PBS), resuspended in medium and dispensed into Roux flasks (Nunc, Wiesbaden, Germany). After 24 hours the medium is changed. The initial passage of confluent cells after 3-5 days is considered as PDL zero. Cells are passaged (1:2 to 1:4) at confluence, using 0.25% trypsin/0.02% EDTA, which is inactivated with 1 mg/ml trypsin-inhibitor. Cumulative PDL is calculated as a function of passage number and split ratio. PDLs of RPTEC/TERT1 cells are indicated as PDL post transfection (PDLpT).

In order to show that these cells have retained the characteristics of primary cells, their ability to form tight junctions and domes is tested, as described by Wieser et al., 2008. Furthermore, their response to hormones in terms of cAMP production, as well as the expression or RPTEC specific transport proteins like Megalin/Cubilin is tested as described by Wieser et al., 2008.

1.6. Adipose Tissue Derived Stem Cells (ASCs)

Subcutaneous adipose tissue is obtained during outpatient tumescence liposuction under local anesthesia. ASCs are isolated as described (Wolbank et al., 2009) and cultured in DMEM-low glucose/HAM's F-12 supplemented with 2 mM L-glutamine, 10% fetal calf serum (FCS, PAA or PAN, Gibco), 100 U/mL penicillin, 0.1 mg/mL streptomycin and 1 ng/mL recombinant human basic fibroblast growth factor (rhFGF, R&D Systems) at 37° C., 5% $CO_2$ and 95% air humidity to a subconfluent state.

A retroviral transfection system, as described above, is chosen for introduction of hTERT. Gene transfer is performed at early PD according to the manufacturer's instructions (Clontech Laboratories Inc.). 24 hours post transduction, transfectants are selected using Geneticin Sulfate G418 and arising cell clones are grown as mass culture.

Besides a large panel of surface markers (CD14, CD34, CD45, CD73, CD90, CD105, etc), the ability to differentiate into adipogenic or osteogenic lineage is tested.

1.7. Amnion-Derived Stem Cells

Human placentae are obtained during caesarean sections. Amniotic membrane is peeled off the placenta by blunt dissection and washed several times in phosphate-buffered saline (PBS). hAMSCs are isolated as and cultured in EGM-2 (Lonza, Verrier, Belgium) at 37° C., 5% $CO_2$, and 95% air humidity to a sub-confluent state. Besides a large panel of surface markers (CD14, CD34, CD45, CD73, CD90, CD105, etc) the ability to differentiate into adipogenic or osteogenic lineage is tested, as described (Wolbank et al., 2009).

1.8. Human Exfoliated Proximal Tubular Epithelial Cells (HEPTECs)

300 ml-500 ml of mid-stream urine of healthy and diseased (cancer or diabetes) individuals is collected. Cells are pelleted by centrifugation at 4.000 rpm for 20 min at 4° C. Supernatant is carefully removed. Cells are washed with ice-cold PBS and seeded onto culture dishes in DMEM/Ham's F12, and 10% FCS and incubated at 5% $CO_2$, 37° C. Passaging is performed using 0.25% trypsin in 1 mmol/l EDTA. FCS concentration is reduced 0.5% FCS. HEPTECs are selected using flow cytometry or MACS beads after 1-3 passages using antibodies selective for CD13/aminopeptidase N labelled with FITC and further cultivated. The tubular epithelial cell phenotype is confirmed as for RPTECs (see above). HEPTECs may also be immortalized according to the method recently published by (Wilmer et al., 2010)

1.9. Human Exfoliated Fibroblastoid Cells (HEFCs)

300 ml-500 ml of mid-stream urine of healthy and diseased (cancer or diabetes) individuals is collected. Cells are pelleted by centrifugation at 4,000 rpm for 20 min at 4° C. Supernatant is carefully removed. Cells are washed with ice-cold PBS and seeded onto culture dishes in DMEM/Ham's F12 1:1, 4 mM L-Glutamine, 10% FCS and incubated at 5% $CO_2$, 37° C. Passaging is performed using 0.25% trypsin in 1 mmol/l EDTA. The fibroblastoid phenotype is confirmed as described above.

1.10. Human Fetal Hepatocytes (HHCs)

Fetal tissues from elective terminations at 22-24 weeks of gestation are obtained. Fetal livers are digested in 0.05% collagenase for 30 minutes at 37° C. Dissociated cells are passed through 80 μm dacron mesh, washed, and pelleted at 500 g for 4 minutes at 4° C. The cell pellet is resuspended in Dulbecco's modified Eagle's medium (Invitrogen, Carlsbad, Calif.), containing 5 μg/mL insulin (Sigma, St. Louis, Mo.), 2.4 μg/mL hydrocortisone (Sigma), 10% FCS (Invitrogen). Primary cultures are established in tissue culture dishes at 4×10³ cells per cm² in a humidified 5% $CO_2$ atmosphere. Cultures were passaged at a ratio of 1:4 thereafter (Wege et. al., 2003).

Immortalization is performed using pLXSN-hTERT retroviral transduction as described above. The presence of hepatocyte markers is confirmed e.g. by determining expression of hepatocyte marker proteins like HGFR, C/EBP, albumin, and HNF-4. Functionality testing might include testing for glycogen storage ability, glucose-6-phosphatase activity, and production of urea. Finally, inducibility of members of the CYP 1 and 2 protein families, proteins involved in hepatic drug metabolism that are switched on upon various stressors (e.g. ethanol, aromatic-compounds), can be compared to parental cells.

1.11. Human Myoblasts

Minced muscle fragments (from patients with muscular dystrophy) are incubated in a 100 mm dish containing 4 mL of medium, sufficient to cover the bottom but preventing floating of the fragments thus removing their contact with the dish. Cultures are initiated in modified Dulbecco's modified Eagle's medium, supplemented with 20% fetal bovine serum, 30 mM HEPES and 5 ng/mL HGF (R&D systems, Minneapolis, Minn., USA), on dishes coated with 0.1% pig skin gelatin (Sigma-Aldrich, St. Louis, Mo., USA). Outgrowth of satellite cells is more robust when cultured in a 2% oxygen chamber than in room oxygen (20%). Cells are sub-cultivated when just confluent. The final culture conditions consist of the above basal medium supplemented with dexamethasone, zinc sulphate ($ZnSO_4$) vitamin B12.

Immortalization is achieved using retroviral hTERT constructs combined with the same viral vector pLXSN containing the cDNA of CDK4 in analogy to the method described by (Zhu et al., 2007). Myoblast phenotype is confirmed using indirect immuno-fluorescence microscopy or flow cytometry for myoblast marker proteins desmin, MyoD, MF20, and Pax7 as well as myotube formation.

1.12. Induced Pluripotent Stem Cells (iPSCs) and Cells Differentiated from IPSCs Induced pluripotent stem cells or iPSCs are stem cell-like cells derived from reprogrammed somatic cells, e.g. fibroblasts or epithelial cells, or urine-derived cells. Reprogramming to obtain iPS cells is achieved by simultaneously expressing 2-4 ES cell specific transcriptional factors including Oct4, Sox2, Myc and Klf4/Lin28 using viral vectors (lentivirus or retrovirus). The reprogramming process takes 15-30 days. First, the somatic cells such as fibroblast cells or urine-derived cells are infected with a mixture of viral particles expressing the 2-4 stem cell factors (Oct4, Sox2, Myc and Klf4/Lin28). The infected cells are then seeded on mouse embryonic fibroblast (MEF) feeder cells and cultured in ES cell medium. After 10-15 days, ES like colonies of cells appear, can be picked and expanded. Reprogramming can also be done without using MEF feeder cells.

The obtained iPSCs are then differentiated into specific cell types (neuronal cells, endothelial cells, osteoblasts, osteoclasts, etc.), using the respective culture conditions for inducing specific immortalization and then immortalized by overexpression of hTERT, viral oncogenes or combinations thereof. Characteristics of the resulting cells are tested depending on the differentiated cell type. By way of example, differentiation into the osteogenic lineage is analysed by alizarin red staining as well as adipogenic differentiation by the accumulation of lipid droplets while neuronal differentiation is confirmed. Differentiation into liver cells useful as toxicity index cells can be performed according to known methods, e.g. as described by Song et al., 2009. In brief, differentiation is initiated by cultivating the hUiPSCs for 5 days with 100 ng/ml activin A in RPMI/B27 medium under standard cell culture conditions. Then the cells are incubated for 5 days with 20 ng/ml BMP4/10 ng/ml FGF-2 in RPMI/B27, then 5 days with 20 ng/ml HGF in RPMI/B27 supplement, and finally for 5 days with 20 ng/ml Oncostatin-M in Hepatocyte Culture Medium (Lonza) supplemented with SingleQuots (without EGF). As marker(s) for hepatocytes, production of albumin, glycogen and/or the asialoglycoprotein receptor are tested.

2. Use of Cell Panels in "Differential Drug Screening" Assays

2.1. Testing Efficacy and Toxicity of Anti-Tumor Drug Candidates

In this screening experiment, a cell panel is used that consists of four different sets of cells.

Cell set "ECs" consists of five cell samples, isolated from human umbilical veins as described above. Each of the cell samples is derived from a different donor, has been immortalized by telomerase, cultivated as mass culture and tested for endothelial-specific characteristics (as described above, like expression of ICAM and PECAM, ability to form neoangiogenic webs on matrigel and response to TNF-α and LPS).

Cell set "RPTECs" consists of five cell samples, isolated from human kidney as described above, from five different healthy donors, immortalized by telomerase and cultivated as mass culture. The RPTEC phenotype has been confirmed as described above in each of the cell lines (expression of γ-GGT and aminopeptidase N; ability to form tight junctions and domes; response to hormones in terms of cAMP production, expression or RPTEC specific transport proteins like megalin/cubilin).

Cell set "HHCs" contains human fetal hepatocytes, immortalized by telomerase as described (Wege et al., 2003) of five different healthy donors, cultivated as mass cultures. Again, markers of liver specific functionality are confirmed including expression of hepatic growth factors, growth factor receptors, albumin, glucose-6-phosphatase, cytochrome P450 (CYP) expression profile. Furthermore, their functionality in regard to glycogen synthesis and urea production is tested.

Cell set "HDFs" consists of five cell samples, isolated from human skin of five different healthy donors, immortalized by telomerase and cultivated as mass culture. The fibroblastoid phenotype has been confirmed as described above in each of the cell lines (presence of fibroblast marker proteins like fibroblast-specific protein 1 (FSP1) andand prolyl-4-hydroxylase versus absence of epithelial marker proteins like immuno-reactivity to pan cytokeratin).

2.1.1. Testing the Effect on Epithelial Cell Growth and Angiogenesis

In order to test the suitability of drug candidates for further clinical development, the compounds are tested for their ability to inhibit endothelial cell growth using an MTT assay or to inhibit neovascularisation using in vitro angiogenesis assays in a dose and time dependent manner. The in vitro angiogenesis assay on matrigel (Becton Dickinson) is performed in 96-well cell culture plates according to the manufacturer's instruction using 5×10⁴ cells/cm². Cells are incubated at 37° C. in a humidified atmosphere containing 5% $CO_2$. High content screening is performed at 6 h and 24 h post inoculation onto matrigel and form and length of neoangiogenic webs are analysed to assess neoangiogenic potential.

Celastrol (Salminen et al., 2010) and Morelloflavone (Pang et al., 2009), two recently described inhibitors of tumor-associated angiogenesis, are used as examples for drug candidates as test compound in this experiment. High content screening (HCS) systems (Cellomics, ThermoFisher or Operette, Perkin Elmar) are employed, using cell set "ECs" containing immortalized endothelial cells obtained from five different donors. The cells are seeded into 96 well plates compatible with HCS systems per donor at a cell number of 300 cells per well and 30000 cells per well. Using these different cell densities, effects of the compounds on confluent as well as subconfluent cells is evaluated. The cells are allowed to adhere overnight. Using different doses of the drug candidates ranging between 0.01 to 1 μg/ml for celastrol and 1-400 μmol/ml Morelloflavone, a concentration and time range (between 12 to 48 h) of highest efficacy is then established. Inhibition of endothelial cell growth is monitored by counting cell numbers using high content screening as well as MTT assays as end-point measurements as well as in vitro neoangiogenesis as described above.

2.1.2. Testing Toxicity

Having established time and dose ranges that efficiently reduce endothelial cell growth, these ranges are analysed for toxicity on cell set "RPTECs" (immortalized renal proximal tubular epithelial cells from 5 different donors) as model cells for renal toxicity as well as on cell set "HHFs", immortalized fetal liver cells as model cells for liver toxicity. Therefore, between 300 and 30000 cells per well are seeded into each well of 96 well plates. After overnight adherence, Celastrol or Morelloflavone at different effective doses is applied. Toxic effects are analysed after 12 to 72 hours by measuring apoptotic and necrotic cell death by annexin V/PI staining in a high content screening system. In order to test for toxic effects of processed forms of the compounds that are generated by fetal liver cells or RPTECs, supernatants of Celastrol- or Morelloflavone-treated cells versus supertnatants from untreated cells are applied to the cell set "ECs" and "HDFs" in two different dilutions to test for toxicity of potentially bioconverted products derived from the drugs. Again, viability, apoptosis and necrosis are determined 12-72 h later by the methods outlined above.

Cell death of RPTECs, fetal liver cells, fibroblasts and endothelial cells in all five donors has to be no more than 25%, preferably no more than 10% higher as compared to non-treated or vehicle-treated controls at doses efficient for inhibiting endothelial cell growth and formation of neoangiogenic webs of five different donors in order to recommend the compounds for further drug development.

2.2. Testing Efficacy and Toxicity of Anti-Diabetic Drug Candidates

In this assay the cell panel consists of four sets of cells.

Cell set "Myo" contains five cell samples, isolated from human muscle biopsies as described above. Each of the cell samples derives from a different donor, has been immortalized by telomerase, cultivated as mass culture and has been tested for myoblast specific characteristics (as described above, like desmin, MyoD, MF20, and Pax7 as well as myotube formation).

Cell set "ASCs" contains five ASC cell samples, isolated from human adipose tissue by liposuction as described above. Each of the cell samples derives from a different donor, has been immortalized by telomerase and cultivated as mass culture. For the assay, ASCs are employed that have been confirmed to express functional insulin receptor.

Cell set "RPTECs" consists of five cell samples, isolated from human kidney of five different donors as described above, immortalized by telomerase and cultivated as mass culture. The RPTEC phenotype has been confirmed as described above in each of the cell lines (expression of γ-GGT and aminopeptidase N; ability to form tight junctions and domes; response to hormones in terms of cAMP production, expression or RPTEC specific transport proteins like Megalin/Cubilin).

Cell set "hUiPSCs-Hep" contains human urine-derived human iPSCs (hUiPSCs), from 5 different donors, differentiated into hepatocytes. hiUPSCs are generated and differentiated as described above. Again, markers of liver specific functionality are confirmed including expression of hepatic growth factors, growth factor receptors, albumin, glucose-6-phosphatase, cytochrome P450 (CYP). Furthermore the cells' functionality in regard to glycogen synthesis and urea production is tested.

2.2.1. Testing the Effect on Insulin-Receptor Activation

Recently, a series of hydroxyfuroic acid compounds has been identified as potential novel oral anti-diabetics (Tsai and Chou, 2009). Dose and time dependence of insulin-receptor activation by the individual hydroxyfuroic acid compounds is analysed using the cell sets "Myo" and "ASCs" containing immortalized human myoblasts and ASCs, each of the cell sets containing cell samples from five different donors. 300-3000 cells per well are seeded into multititer well plates to evaluate effects in dependence of cell confluence. After attachment over night, hydroxyfuroic acid compounds are added in a concentration range of 10-20 μM. Insulin-receptor activity is assessed using Fura-2, which indicates insulin dependent $Ca^{2+}$ flux into the cytoplasm by fluorescence measurement using high content screening. Alternatively, insulin receptor tyrosine kinase activity is analysed as follows: Cells are rinsed with phosphate buffered saline (PBS) three times and starved in serum free medium for 2 hours before being stimulated with desired concentration of insulin or test compounds for 20 minutes. Test compounds are pre-dissolved and serially diluted when necessary. Stimulated myoblasts or ASCs are then lysed. The lysates are transferred to Flexible Assay Plate precoated with Ab-3 antibody recognizing a subunit of insulin receptor. The well is then rinsed and 10 μl of tyrosine kinase reaction mixture (50 mM HEPES, pH 7.4, 5 mM MgCl2, 5 mM MnCl2, 1 mg/mL polyGlu/Tyr and 250,000 cpm γ-P33 ATP/well) is added. The reaction is carried out at room temperature for 40 minutes and terminated by adding 50 μl ice cold 100 mM phosphoric acid. 50 μl thereof are then transferred to an inch square P81 paper. The P81 paper is air dried and then rinsed in Millipore water five times to remove leftover radioactive ATP and product ADP. 5 mL of scintillation cocktail is added to the paper before the count is read in a liquid scintillation counter.

2.2.2. Testing Toxictiy

Having established optimal dosage ranges, toxicity of the compounds is analysed using the cell sets "RPTECs" and "hUiPSCs-Hep" containing immortalized renal proximal tubular epithelial cells from 5 different donors as model cells for renal toxicity as well as from hUiPSCs, from 5 different donors, differentiated hepatocytes as model cells for liver toxicity, as described above for the substances that inhibit angio-genesis. Toxic effects of hydroxyfuroic acid compounds or their processed forms are analysed by measuring apoptotic and necrotic cell death by annexin V/PI staining in a high content screening system as described above.

Cell death of RPTECs and hUiPSCs-Hep cells from all five donors has to be no more than 25%, preferably no more than 10% higher as compared to non-treated or vehicle-treated controls at doses efficient for activating insulin receptor signalling in cells from 5 different donors.

REFERENCES

Bodnar et al., 1998, Science 279, 349-352
Cai et al., 2010, J Biol Chem 285, 11227-11234
Chang et al., 2005, Exp Cell Res 309, 121-136
Delvenne et al., 2001, Vaccine 19, 2557-2564
Elenbaas et al., 2001, Genes Dev. 2001 Jan. 1; 15(1):50-65
Esteban et al., 2010, Cell Stem Cell 6, 71-79
Forsyth et al., 2004, Neoplasia; 6:258-265
Garcia-Escudero et al., 2010, Mol Ther 18, 394-403
Hooijberg et al., 2000, J. Immunol. 2000; 165:4239-4245
Griendling et al., 1988, Clin Exp Pharmacol Physiol 15, 105-112
Kowolik et al., 2004, Oncogene 23: 5950-5957
Lowry and Plath, 2008, Nat Biotechnol 26, 1246-1248
Meineke et al., 2004, Strahlenther Onkol 180, 102-108
O'Malley et al., 2009, Curr Opin Biotechnol 20, 516-521
Orosz et al., 2004, In Vitro Cell Dev Biol Anim 40: 22-34
Pang et al., 2009, Cancer Res 69, 518-525
Racusen et al., 1997, J Lab Clin Med 129: 318-329
Rensen et al., 2007, Neth Heart J 15, 100-108
Ryan et al., 1994, Kidney Int 45: 48-57
Salminen et al., 2010, Biochem Biophys Res Commun 394, 439-442
Song et al., 2009, Cell Res. 2009 November; 19 (11):1233-42.
Stadler et al., 2007, Cytotherapy 9, 488-498
Takahashi and Yamanaka, 2006, Cell, 126: 663-676
Tsai and Chou, 2009, J Biomed Sci 16, 68
Vaughan et al., 2006, Differentiation April; 74(4):141-8
Voglauer et al., 2006, Exp Cell Res 312, 746-759
Voglauer et al., 2005, Int J Oncol 26, 961-970
Wege et al., 2003, Gastroenterology 124, 432-444
Wieser et al., 2008, Am J Physiol Renal Physiol 295, F1365-1375
Wiesner et al., 2008, PLoS One 3, e1464
Wilmer et al., 2010, Cell Tissue Res 339, 449-457
Wolbank et al., 2009, Tissue Eng Part A 15, 1843-1854
Zhu et al., 2007, Aging Cell 6, 515-523

The invention claimed is:
1. A method for preparing a panel of mammalian cells for testing efficacy or toxicity by means of a bioassay, said method comprising the steps of:
i) providing immortalized primary cells from tissues and/or organs that are relevant for testing efficacy or toxicity of an agent, wherein said tissues and/or organs are from one or more healthy and/or diseased donors, and wherein the cells are selected from the group consisting of fibroblasts, epithelial cells, myoblasts, endothelial cells, cardiomyocytes, blood cells, keratinocytes, osteoblasts, urothelial cells, fetal liver cells, Schwann cells, neural progenitor cells, Sertoli cells, and human exfoliated proximal tubular epithelial cells;
ii) selecting, from the cells obtained in step i), cells that are, with respect to at least one predetermined morphological or functional property that is essential for the read-out of said bioassay, identical to corresponding primary cells, wherein the property is selected from the group consisting of expression of a target or marker molecule, phenotypic differentiation potential, neoangiogenic potential, uptake capacity for certain molecules, apoptotic capacity, capacity for formation of tight junctions and/or domes, expression of aminopeptidase N, cAMP induction by parathyroid hormone, sodium-dependent phosphate uptake, transport of molecules mediated by megalin and/or cubilin, and response to inflammatory signals;
iii) providing cell samples comprising the cells selected in step ii), wherein the cell samples are derived from at least five donors or are from at least two different organs and/or tissues of the same donor;
iv) providing one or more cell samples selected from the group consisting of kidney cells, liver cells, blood cells, endothelial cells, and skin cells;
v) combining different cell samples of step iii) to form sets of cell samples;
vi) combining sets of cell samples of step v) with cell samples of step iv) to form a panel of cell samples; and
vii) testing the efficacy or toxicity of the agent with the panel of cell samples of step vi).

2. The method of claim 1, wherein said bioassay is a cytotoxicity assay and wherein the cells in the samples according to step iv) are one or more cells samples selected from the group consisting of kidney cells, liver cells, blood cells, endothelial cells, and skin cells.

3. The method of claim 1, wherein step iii) comprises providing cell samples comprising the cells selected in step ii), and wherein the cell samples are derived from at least five donors.

4. The method of claim 1, wherein step v) comprises combining cell samples from at least five donors to form sets of cell samples.

* * * * *